United States Patent [19]

Tsuno et al.

[11] Patent Number: 4,732,976
[45] Date of Patent: Mar. 22, 1988

[54] 3,3-NEOTREHALOSADIAMINE ANTIBIOTIC AND PRODUCING IT WITH NOVEL MICROORGANISM

[75] Inventors: Takashi Tsuno, Higashimurayama; Masataka Konishi, Kawasaki, both of Japan

[73] Assignee: Bristol-Myers Company, New York, N.Y.

[21] Appl. No.: 806,880

[22] Filed: Dec. 9, 1985

[51] Int. Cl.$^4$ .................. C07G 11/00; C07H 15/00; C07H 17/00; A61K 35/00
[52] U.S. Cl. .................. 536/16.8; 536/18.7; 536/55; 536/17.2; 514/25; 424/116
[58] Field of Search .......... 536/18.7, 55, 16.8, 536/17.2; 514/25; 424/116

[56] References Cited

U.S. PATENT DOCUMENTS 4,260,683  4/1981  Kawaguchi et al. .................. 435/74
4,276,412  6/1981  Dolak et al. ........................ 536/16.8
4,482,707  4/1984  Sakakibara et al. .................. 435/74

FOREIGN PATENT DOCUMENTS 7029486  9/1970  Japan .................. 536/55

OTHER PUBLICATIONS

Dolak et al.; J. Antibiotics 33:690–694 (1980).
Naganawa et al.; J. Antibiotics 27:145–146 (1974).
Uramoto et al.; J. Antibiotics 20A:236–237 (1967).

Primary Examiner—Ronald W. Griffin
Assistant Examiner—Nancy S. Carson
Attorney, Agent, or Firm—David M. Morse

[57] ABSTRACT

3,3'-Neotrehalosadiamine antibiotic is prepared by fermentation of *B. pumilus* K169-B91 (ATCC No. 53206) in a nutrient medium preferably comprising soybean meal, corn starch, calcium carbonate and magnesium sulfate. The antibiotic and pharmaceutically acceptable salts and hydrates thereof and compositions containing these are useful to treat bacterial infections in mammals.

3 Claims, 3 Drawing Figures

3,3'-NEOTREHALOSADIAMINE ANTIBIOTIC AND PRODUCING IT WITH NOVEL MICROORGANISM

TECHNICAL FIELD

This invention is directed to a novel antibiotic, to a novel microorganism for producing the antibiotic, to a method of producing the antibiotic utilizing the microorganism, to compositions containing the antibiotic and to a method of treating bacterial infections with the antibiotic.

BACKGROUND OF THE INVENTION

Several aminodisaccharide antibiotics have previously been reported in literature. These compounds include: 3-trehalosamine reported by L. A. Dolak et al., *J. Antibiotics* 33:690–694 (1980); 4-trehalosamine reported by H. Naganawa et al., *J. Antibiotics* 27:145–146 (1974); and mannosyl glucosaminide, which is linked through a 1,1-glycoside linkage, reported by M. Uramoto et al., *J. Antibiotics* 20A:236–237 (1967).

All of these aforementioned aminodisaccharide antibiotics are $\alpha,\alpha'$-glycosides of an amino sugar and a neutral sugar.

SUMMARY OF THE INVENTION

The novel antibiotic herein is 3,3'-neotrehalosadiamine which has been determined to have the structural formula

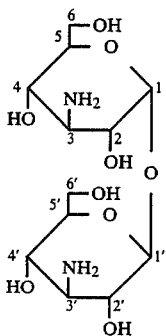

and its nontoxic pharmaceutically acceptable salts or hydrates. This is unique in being an aminodisaccharide which is the 1,1'-glycoside of two amino sugars rather than of an amino sugar and a neutral sugar.

The antibiotic herein is readily produced in a recoverable quantity by culturing of the novel microorganism *Bacillus pumilus* K169-B91 (ATCC No. 53206) under aerobic conditions at a temperature ranging from 15° to 55° C. in a nutrient media and separating and recovering of the antibiotic. The acid addition salts and hydrates are readily made up by methods known in the art.

The antibiotic herein and compositions containing it together with a suitable pharmaceutically acceptable carrier are effective against a variety of microorganisms and are administered to mammals for treatment and control of antibacterial infections in an amount suitable for such treatment, i.e. in a therapeutically effective amount.

DETAILED DESCRIPTION

Figure 1:
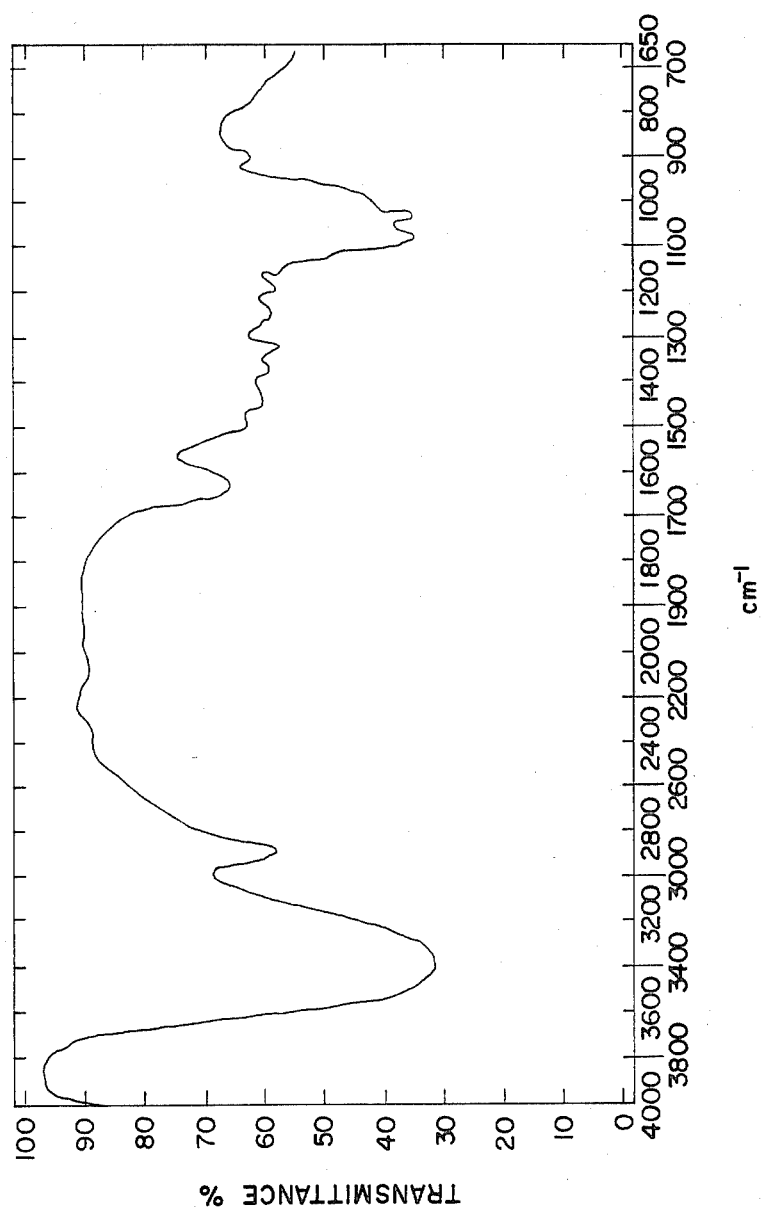
FIG. 1—Infrared absorption spectrum of 3,3'-neotrehalosadiamine in KBr.

The free base antibiotic herein, i.e. 3,3'-neotrehalosadiamine is characterized by physico-chemical properties as set forth in Table 1 below. In this table the IR spectrum referred to is that depicted in FIG. 1, the $^{13}$C-NMR spectrum is that depicted in FIG. 2 and the $^1$H-NMR spectrum is that depicted in FIG. 3.

TABLE 1

| Nature | White amorphous powder |
|---|---|
| M. p. | 116–119° C. (dec.) |
| $[\alpha]_D^{24}$ | +36° (c 0.4, $H_2O$) |
| Elemental analysis % | |
| Calcd for $C_{12}H_{24}N_2O_9$ | C 42.35, H 7.11, N 8.23 |
| Found | C 42.54, H 7.43, N 8.60 |
| EI-MS | m/z 340 (molecular ion) |
| pKa' | 7.90 (in $H_2O$) |
| Color reactions | |
| Positive | Ninhydrin, anthrone |
| Negative | Tollen's, $FeCl_3$ |
| UV (MeOH) | end absorption |
| IR (KBr) | 3500–3200, 1620, 1440, 1325, 1080, 1030 cm$^{-1}$ |
| $^1$H-NMR $\delta$ in ppm (60 MHz, in $D_2O$, pD $\geq$ 2.0) | 3.2–4.2 (12H, m), 4.78 (1H, d, J=8.0 Hz) and 5.33 (1H, d, J=3.5 Hz) |
| $^{13}$C-NMR $\delta$ in ppm (20 MHz, in $D_2O$, pD = 2.0) | 55.9 (d), 58.6 (d), 60.9 (t), 61.0 (t), 66.7 (d), 66.8 (d), 68.9 (d), 71.3 (d), 72.1 (d), 77.6 (d), 92.0 (d) and 96.9 (d) |

In particular, on acetylation with acetic anhydride and pyridine, 3,3'-neotrehalosadiamine afforded an octaacetyl derivative which exhibited the molecular ion at m/z 676 and strong fragment ions at 616 (M$^+$-AcOH), 556 (M$^+$-2AcOH), 482 (556-AcOCH$_3$) and 330 (oxionium ion of aminohexose). On heating under reflux for 40 hours with methanolic hydrogen chloride (1.5N), chromatographing on Amberlite CG-50 (NH$_4^+$) to isolate the $\alpha$- and $\beta$-methyl glycosides of the sugar, and purifying by Sephadex LH-20 chromatography, the $\alpha$-methyl glycoside (Ia) exhibited $[\alpha]_D^{24}$: +130° (C 0.4, $H_2O$) and the $\beta$-methyl glycoside (Ib) exhibited $[\alpha]_D^{29}$: −28° (C 0.4, $H_2O$). In the $^1$H-NMR spectra in $D_2O$, the anomeric proton of $\alpha$-methyl glycoside (Ia) appeared as a doublet (J: 3.5 Hz) at $\delta$: 4.75 ppm while that of $\beta$-methyl glycoside (Ib) resonated at a higher field with a larger coupling constant ($\delta$: 4.41 ppm, d, J: 7.5 Hz). These compounds were identified as methyl 3-amino-3-deoxy-$\alpha$-D-glucopyranoside (Ia) and its $\beta$-anomer (Ib). No fragment other than the $\alpha$- and $\beta$-methyl glycoside was found in the acid hydrolyzate indicating 3,3'-neotrehalosadiamine is composed of two moles of 3-amino-3-deoxy-D-glucose. The fact that 3,3'-neotrehalosadiamine was negative to Tollen's reaction indicated an 1,1'-glycoside structure for the antibiotic. The anomeric protons observed at $\delta$: 5.33 ppm (J: 3.5 Hz) and 4.78 ppm (J: 8.0 Hz) are assignable to those of $\alpha$- and $\beta$-glycoside, respectively. In the $^{13}$C-NMR spectrum determined at pD=11.0, the carbon signals assigned to C-2 ($\delta$: 72.9 ppm), C-2' (75.6), C-4' (70.7) and C-4 (70.6) underwent a $\beta$-shift (ca. 4–5 ppm) upon acidification. As in the case of 3-trehalosamine, the C-1 and C-1' carbon signals of 3,3'-neotrehalosadiamine appeared at rather high field.

As previously indicated the 3,3'-neotrehalosadiamine antibiotic herein is produced utilizing a culture of the microorganism Bacillus pumilus K169-B91 ATCC No. 53206.

Cultivation of the culture Bacillus pumilus K169-B91 ATCC No. 53206 may be conducted under conditions similar to those employed in previous fermentations yielding aminodissaccharide antibiotics as displayed in J. Antibiotics 33: 690–694 (1980); J. Antibiotics 27: 145–146 (1974); and J. Antibiotics 20A: 236–237 (1967). Cultivation preferably takes place in aqueous nutrient media under submerged aerobic conditions with agitation at a temperature of 15° to 55° C. Nutrient media useful for cultivation include a source of assimilable carbon such as sugars, starches and glycerol; a source of organic nitrogen such as casein, enzymatic digest of casein, soybean meal, cotton seed meal, peanut meal, wheat gluten, soy flour, meat meal and fish meal. A source of growth substances such as grain solubles and yeast extract as well as salts such as sodium chloride and calcium carbonate and trace elements such as iron, magnesium, zinc, cobalt and manganese may also be utilized with advantageous results. If excessive foaming is encountered during fermentation, antifoam agents such as vegetable oils or silicones may be added to the fermentation medium. Aeration of the medium in tanks for submerged growth is preferably maintained at the rate of about ½ to 2 volumes of sterile free air per volume of fermentation broth per minute forced into the broth through a sparger. Agitation may be maintained by means of agitators generally familiar to those skilled in the fermentation art. The rate of agitation depends on the type of agitator employed. A shake flask is usually run at 150 to 200 cycles per minute whereas a fermentor is usually run at 100 to 300 revolutions per minute. Aseptic conditions must, of course, be maintained through the transfer of the organism and throughout its growth.

Inoculum for the preparation of the antibiotic according to this invention may be obtained by employing growth from a slant of the culture. The growth may be used to inoculate either shake flasks or inoculum tanks seeded from the shake flasks. Growth in shaken flasks will generally have reached its maximum in 2 to 4 days whereas inoculum in submerged inoculum tanks will usually be at the most favorable period in 1½ to 3 days.

The progress of antibiotic production during fermentation and the bioactivity of the fermentation broth can be monitored by biological assay of the broth employing a sensitive strain of Staphylococcus aureus, Bacillus subtilis or Klebsiella pneumoniae. S. aureus 209P, B. subtilis PCI-219 and K. pneumoniae No. 126 are suitable strains for this purpose. The disc agar plate assay technique is employed in which the zone of inhibition surrounding a filter paper disc saturated with the broth is used as a measure of antibiotic potency. Also, thin-layer chromatography employing silica gel is a useful tool for analyzing the antibiotic produced in fermentation media and the composition of crude and purified materials extracted from the fermentation broths. The Merck silica gel 60 F. 254 chromatograms are developed with chloroform./methanol/conc. ammonia (1:3:2) or 10% ammonium acetate/methanol (1:1). The antibiotic compound is visualized by spraying with ninhydrin or anthrone reagent and heating the TLC plate at 80° C. The antibiotic will appear as a spot. The plate can also be overlayed with agar seeded with K. pneumoniae No. 126 and incubated at 37° C. for 16 hours to visualize the antibiotic.

The antibiotic produced by fermentation of B. pumilus K169-B91 ATCC No. 53206 may be separated and recovered by using a weakly acidic ion exchange resin such as Amberlite IRC-50.

Preferably, the culture is inoculated into a medium comprising by weight from about 0.5% to about 5% source of assimilable carbon, from about 0.5% to about 5% source of assimilable nitrogen, from about 0.1% to about 2% of calcium carbonate and from about 0.01% to about 0.5% magnesium source, and sterile water.

Very preferably, the culture is inoculated from a slant into a medium comprising by weight from about 1% to about 3% soybean meal, from about 1% to about 3% corn starch, from about 0.5% to about 2% calcium source (very preferably $CaCO_3$), from about 0.1% to about 0.5% magnesium source preferably magnesium sulfate especially $MgSO_4.7H_2O$, and sterile water.

The antibiotic producing microorganism, strain No. K169-B91, of the present invention was isolated from a soil sample collected in Peru. The microorganism was found upon examination to be an aerobic, gram-positive, spore-forming rod bacterium classified as belonging to the genus Bacillus. The morphological, cultural and physiological characteristics of the microorganisms indicated that strain No. K169-B91 is classified into Bacillus pumilus Meyer and Gottheil 1901. Thus the strain of the instant invention is herein designated as Bacillus pumilus K169-B9.

The morphological observations of strain No. K169-B91 can be summarized as follows. The vegetative cells were straight or occasionally bent oblong or short rod which ranged in size from $0.6–0.7\times1.5–3.0$ μm and were motile and gram-positive. The strain had elliptical spores ranging in size from $0.7–0.8\times1.0–1.5$ μm having a central position and a distension of sporangia which was either not swollen or occasionally swollen.

The strain No. K169-B91 was incubated on nutrient agar for two days at 28° C. The cultural characteristics of the strain colony were circular and raised having an entire or somewhat irregular margin, an opaque density and a smooth surface. the strain colony had no or scant viscosity, was pale yellow in color and no swarming was noted. The growth temperature of the colony was effective in a range from 15° to 55° C. having maximal growth between 30°–45° C. and no growth at 10° C. or 60° C. The natural pH of the colony was maintained which normally ranged from 5.0 to 10.5.

The physiological characteristics of strain No. K169-B91 are displayed in Table 2 where they are compared with data recorded from characteristics of Bacillus pumilus.

TABLE 2

| | Strain No. K169-B91 | Bacillus pumilus |
|---|---|---|
| Catalase | + | + |
| V-P reaction | + | + |
| Growth in anaerobic agar | − | − |
| Growth at 50° C. | + | + |
| Growth in 7% NaCl | + | + |
| Gas from glucose | − | − |
| Reduction of $NO_3$ to $NO_2$ | − | − |
| Hydrolysis of starch | − | − |
| Growth at 65° C. | − | − |
| pH < 6.0 in V-P broth | +(pH 5.2) | + |
| Acid from | | |
| glucose | + | + |

TABLE 2-continued

|  | Strain No. K169-B91 | Bacillus pumilus |
|---|---|---|
| xylose | + | + |
| arabinose | − | + |
| Hydrolysis of casein | + | + |
| Growth in 0.001% lysozyme | + or ± | v |

Abbreviations
+: positive,
−: negative,
±: doubtful
v: variable

The new culture *Bacillus pumilus* K169-B91 was submitted on July 24, 1985, to the American Type Culture Collection, Rockville, Md., and given the designation *Bacillus pumilus* K169-B91 ATCC No. 53206. The permanency of the deposit of this culture at The American Type Culture Collection at Rockville, Md., and ready accessibility thereto by the public are afforded throughout the effective life of the patent in the event the patent is granted. Access to the culture is available during pendency of the application under 37 C.F.R. 1.14 and 35 U.S.C. 112. All restrictions on the availability to the public of the culture deposited will be irrevocably removed upon granting of the patent.

The pharmaceutically acceptable salts of the invention are those in which the anion does not contribute significantly to toxicity of the salt; these are typically acid additional salts.

For purposes of forming salt form of the antibiotics herein, there may be mentioned pharmaceutically acceptable acids such as hydrochloric and other hydrohalic acids, sulphuric, phosphoric, nitric, aliphatic, alicyclic, aromatic or heterocyclic carboxylic acids or sulphonic acids, such as formic, acetic, propionic, succinic, glycolic, lactic, malic, tartaric, citric, ascorbic, maleic, hydroxymaleic or pyruvic, fumaric, benzoic, p-aminobenzoic, anthranilic, p-hydroxy-benzoic, salicylic, or p-aminosalicylic, methanesulphonic, ethanesulphonic, hydroxyethanesulphonic, ethylenesulphonic, halogenobenzenesulphonic acid, toluenesulphonic acid, naphthalenesulphonic acid or sulphanilic acid.

Conventional methods are used to prepare the salts. Thus, admixture of the free base with the selected acid in an inert solvent such as water, ethyl acetate, methanol, dimethylformamide and the like with salt isolation by conventional concentration or crystallization techniques are employed.

As previously indicated the antibiotic herein is useful in controlling antibacterial infections and is preferably administered as compositions including a pharmaceutically acceptable carrier and such compositions constitute a part of the invention. The antibiotic herein and pharmaceutical compositions containing it can be administered orally and parenterally. Examples of parenteral administration are intramuscular, intravenous, intraperitoneal, rectal and subcutaneous administration.

In respect to pharmaceutical compositions containing the antibiotic herein carrier and other ingredients should be such as not to diminish the therapeutic effects of the antibiotic. Suitable dosage forms for oral use are tablets, dispersible powders, granules, capsules, syrups and elixirs. Examples of parenteral forms are solutions, suspensions, dispersions, emulsions, and the like. The compositions for oral use may contain one or more conventional adjuvants, such as sweetening agents, flavoring agents, coloring agents and preserving agents, in order to provide a composition of suitable pharmaceutical elegance. Tablets may contain the active ingredient in admixture with conventional pharmaceutically acceptable excipients including inert diluents such as calcium carbonate, sodium carbonate, lactose and talc; granulating and disintegrating agents such as starch and alginic acid; binding agents such as starch, gelatin and acacia and lubricating agents such as magnesium stearate, stearic acid and talc. The tablets may be uncoated or coated by known techniques to delay disintegration and absorption in the gastrointestinal tract and thereby provide a sustained action over a longer period. Similarly, suspensions, syrups, and elixirs may contain the active ingredients in admixture with any of the conventional excipients utilized for the preparation of such compositions such as suspending agents (e.g., methylcellulose, tragacanth, and sodium alginate), wetting agents (e.g., lecithin, polyoxyethylene stearate) and preservatives such as ethyl p-hydroxybenzoate. Capsules may contain the active ingredient alone or admixed with an inert solid diluent such as calcium carbonate, calcium phosphate and kaolin. The injectible compositions are formulated as known in the art and may contain appropriate dispersing or wetting agents and suspending agents identical or similar to those mentioned above.

The following examples illustrate preparation and testing of 3,3'-neotrehalosadiamine.

EXAMPLE I

Figure 2:
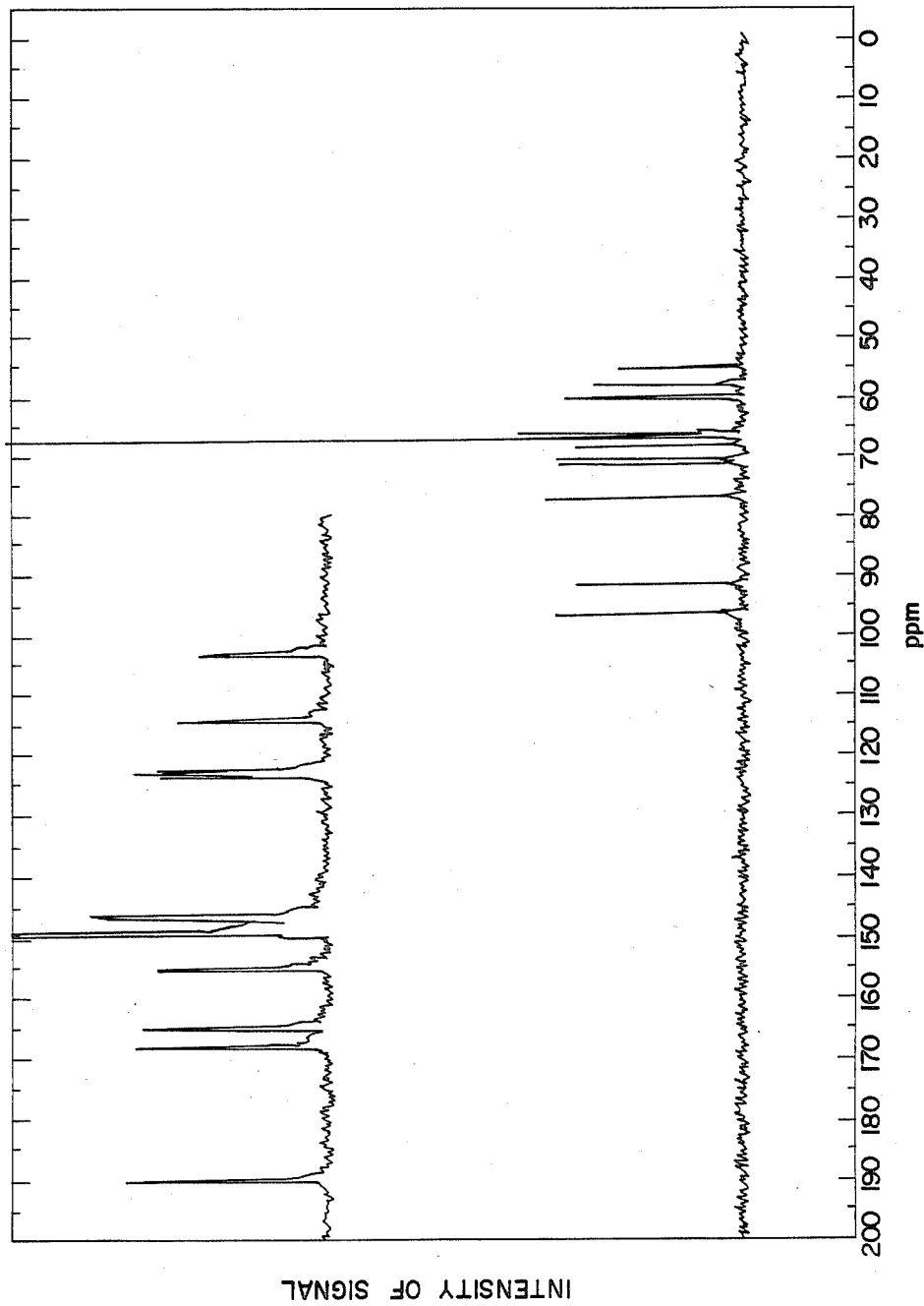
FIG. 2—$^{13}$C-NMR spectrum of 3,3'-neotrehalosadiamine at 20 MHz, in $D_2O$ at PD 2.0.
Figure 3:
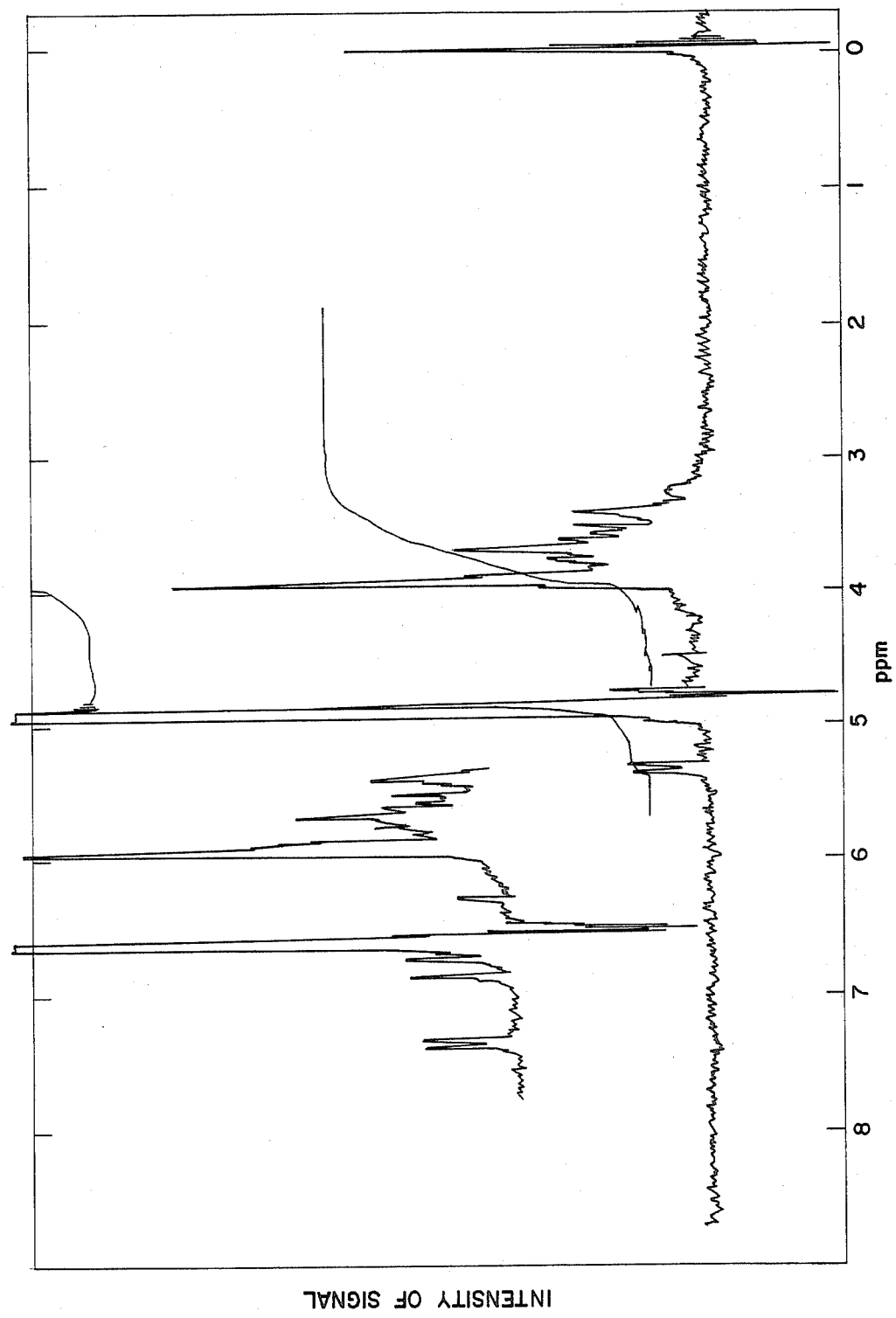
FIG. 3—$^1$H-NMR spectrum of 3,3'-neotrehalosadiamine at 60 MHz, in $D_2O$ at pD 2.0.

A culture of the microorganism *Bacillus pumilus* K169-B91 (ATCC No. 53206) was inoculated from a slant into a medium consisting by weight of soybean meal-3%, corn starch-2%, $CaCO_3$-1% and $MgSO_4.7H_2O$-0.33%, with the remainder being sterile water. Antibiotic production was monitored by the paper disc assay with *K. pneumoniae* No. 126 and reached the maximum of 700 mcg/ml after 42 hours. The harvested broth (10 liters) was clarified using a continuous centrifuge. The mycelial cake was extracted with methanol and the extract concentrated to an aqueous solution. The broth supernate and the concentrate of the methanolic extract were combined, adjusted to pH 7.0 and applied on a column of Amberlite IRC-50 ($NH_4^+/H^+ = 7/3$). The column was developed with water, 0.1N $NH_4OH$, 0.5N $NH_4OH$ and 1N $NH_4OH$, successively. The active fractions were collected and concentrated in vacuo to yield a semi-pure solid which was further chromatographed on Amberlite CG-50 ($NH_4^+$) to afford a homogeneous preparation of 3.6 grams of 3,3'-neotrehalosadiamine. The compound was determined to have spectra as depicted in FIGS. 1-3.

EXAMPLE II

The results in the following table (Table 3) are those found in the cylinder plate assay of 3,3'-neotrehalosadiamine and trehalosamine. In the table BMY-28251 is 3,3'-neotrehalosadiamine.

TABLE 3

| Organism | Inhibition zone** (mm) at 1 mg/ml | | |
|---|---|---|---|
|  | Medium* | BMY-28251 | Trehalosamine |
| *S. aureus* 209P | NA | 21$^w$ | 27$^w$ |
| *B. subtilis* PCI 219 (pH 6.0) | NA | — | 20$^w$ |
| *B. subtilis* PCI 219 (pH 8.0) | NA | 18$^w$ | 23 |
| *K. pneumoniae* #22-3083 | NA | — | — |
| *K. pneumoniae* No. 126 | NA | 19$^w$ | — |

TABLE 3-continued

| | Inhibition zone** (mm) at 1 mg/ml | | |
|---|---|---|---|
| Organism | Medium* | BMY-28251 | Trehalosamine |
| K. pneumoniae No. 126 | #1003 | 23 | 21$^w$ |

*NA: nutrient agar
1003: peptone 10 g, meat extract 5 g and agar 12 g / L
**w: hazy inhibition zone
—: no inhibition zone The 3,3'-neotrehalosadiamine exhibited hazy inhibition zones on nutrient agar plates seeded with *S. aureus* 209P, *B. subtilis* PCI 219 (pH 8.0) and *K. pneumoniae* No. 126 (Kp-126) by the cylinder-plate assay method and clear inhibition zones were obtained on a Kp-126 plate using #1003 medium (Table 3). These test organism were not inhibited by 100 mcg/ml. of 3,3'-neotrehalosadiamine when tested by the agar dilution method. Trehalosamine, which is structually related to 3,3'-neotrehalosadiamine also showed antibacterial activity only by the cylinder-plate assay method althrough its activity profile was somewhat different fromt that of 3,3'-neotrehalosadiamine (Table 3). Unlike the results with trehalosamine, the activity of 3,3'-neotrehalosadiamine was not antagonized by trehalose.

It was found that 3,3'-neotrehalosadiamine was non-toxic to mice at 400 mg/kg when administered intravenously.

Other variations will be evident to those skilled in the art. Therefore, the scope of the invention is intended to be defined by the claims.

We claim:

1. A 3,3'-neotrehalosadiamine compound represented by the structural formula:

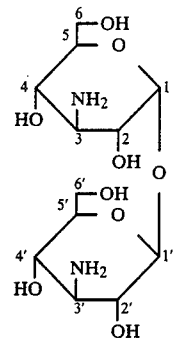

its non-toxic pharmaceutically acceptable salts and hydrates.

2. The compound of claim 1 which is 3,3'-neotrehalosadiamine in free base form.

3. A composition containing the compound of claim 1 and a pharmaceutically acceptable carrier.

* * * * *